(12) United States Patent
Brikmann

(10) Patent No.: US 11,938,523 B2
(45) Date of Patent: Mar. 26, 2024

(54) CONTAINER TREATMENT SYSTEM

(71) Applicant: Krones AG, Neutraubling (DE)

(72) Inventor: Max Brikmann, Neutraubling (DE)

(73) Assignee: KRONES AG, Neutraubling (DE)

( * ) Notice: Subject to any disclaimer, the term of this patent is extended or adjusted under 35 U.S.C. 154(b) by 908 days.

(21) Appl. No.: 16/636,707

(22) PCT Filed: May 29, 2018

(86) PCT No.: PCT/EP2018/064018
§ 371 (c)(1),
(2) Date: Feb. 5, 2020

(87) PCT Pub. No.: WO2019/029858
PCT Pub. Date: Feb. 14, 2019

(65) Prior Publication Data
US 2020/0239172 A1     Jul. 30, 2020

(30) Foreign Application Priority Data
Aug. 9, 2017    (DE) .................. 10 2017 213 861.0

(51) Int. Cl.
*G06F 17/00*     (2019.01)
*A61L 2/18*      (2006.01)
(Continued)

(52) U.S. Cl.
CPC .................. *B08B 3/04* (2013.01); *A61L 2/18* (2013.01); *B25J 5/02* (2013.01); *B25J 9/0018* (2013.01);
(Continued)

(58) Field of Classification Search
CPC ....... B08B 3/04; A61L 2/18; B25J 5/02; B25J 9/0018; B25J 9/1687; B25J 11/0045;
(Continued)

(56) References Cited

U.S. PATENT DOCUMENTS 4,904,153 A * 2/1990 Iwasawa ................ B25J 17/025
                                                         901/17
4,923,352 A * 5/1990 Tamura ............. H01L 21/67772
                                                        414/940
(Continued)

FOREIGN PATENT DOCUMENTS

CN      212764726 U *   3/2021    .......... B29C 49/421
DE      19727355 A1     1/1999
(Continued)

OTHER PUBLICATIONS

Dynatect, Dyanmic equipment protection (Year: 2021).*
(Continued)

*Primary Examiner* — Ronnie M Mancho
(74) *Attorney, Agent, or Firm* — McCoy Russell LLP

(57) ABSTRACT

The present disclosure relates to a container treatment system for the treatment of containers, such as bottles, in the beverage processing industry, comprising a clean room and a container treatment machine arranged therein with at least one exchangeable component, where the container treatment system comprises a robot which is arranged in the clean room and is designed to exchange said exchangeable component, and a corresponding method.

17 Claims, 2 Drawing Sheets

(51) Int. Cl.
| | |
|---|---|
| *B08B 3/04* | (2006.01) |
| *B25J 5/02* | (2006.01) |
| *B25J 9/00* | (2006.01) |
| *B25J 9/16* | (2006.01) |
| *B25J 11/00* | (2006.01) |
| *B25J 13/00* | (2006.01) |
| *B25J 15/00* | (2006.01) |
| *B25J 19/00* | (2006.01) |
| *B25J 21/00* | (2006.01) |
| *B65B 59/04* | (2006.01) |
| *B67C 3/22* | (2006.01) |

(52) U.S. Cl.
CPC ......... *B25J 9/1687* (2013.01); *B25J 11/0045* (2013.01); *B25J 13/00* (2013.01); *B25J 15/0019* (2013.01); *B25J 19/0025* (2013.01); *B25J 21/005* (2013.01); *B65B 59/04* (2013.01); *B67C 3/22* (2013.01); *B67C 2003/228* (2013.01)

(58) Field of Classification Search
CPC .... B25J 13/00; B25J 15/0019; B25J 19/0025; B25J 21/005; B65B 59/04; B67C 3/22; B67C 2003/228; B67C 2003/221; B67C 7/0073; B29C 49/42069; B29C 2049/4697; B29C 49/46; B67B 2201/08
USPC .......................................................... 134/59
See application file for complete search history.

(56) References Cited

U.S. PATENT DOCUMENTS

| | | | | |
|---|---|---|---|---|
| 5,924,833 | A * | 7/1999 | Conboy | H01L 21/67727 414/217 |
| 7,480,976 | B2 * | 1/2009 | Reed | G05B 19/418 29/33 P |
| 8,632,325 | B2 * | 1/2014 | Voth | B65B 55/10 425/522 |
| 9,233,820 | B2 * | 1/2016 | Bernhard | B67B 3/2033 |
| 9,302,896 | B2 * | 4/2016 | Drenguis | B65B 55/08 |
| 2005/0150193 | A1 * | 7/2005 | Bernhard | B67B 3/2033 53/317 |
| 2008/0110011 | A1 * | 5/2008 | Reed | G05B 19/418 29/563 |
| 2013/0040009 | A1 * | 2/2013 | Laumer | B29C 49/42 425/182 |
| 2014/0120235 | A1 * | 5/2014 | Jones | G07F 17/0064 901/30 |
| 2015/0098773 | A1 * | 4/2015 | Rice | G03F 7/70991 414/744.3 |
| 2015/0197415 | A1 * | 7/2015 | Hahn | B67C 7/0006 414/226.02 |
| 2016/0185527 | A1 * | 6/2016 | Greyshock | B65G 35/00 700/218 |
| 2020/0189896 | A1 * | 6/2020 | Raith | B25J 15/0066 |
| 2020/0239172 | A1 * | 7/2020 | Brikmann | B25J 19/0025 |

FOREIGN PATENT DOCUMENTS

| | | | | |
|---|---|---|---|---|
| DE | 10254762 | A1 | 6/2004 | |
| DE | 102009044163 | A1 | 4/2011 | |
| DE | 102010045268 | A1 | 3/2012 | |
| DE | 102011015741 | A1 * | 10/2012 | ............ B23Q 3/155 |
| DE | 102012219886 | A1 | 5/2014 | |
| DE | 102014102630 | A1 | 8/2015 | |
| DE | 202011110939 | U1 | 7/2017 | |
| DE | 102017209838 | A1 * | 12/2018 | .......... B25J 15/0066 |
| DE | 102017213861 | A1 * | 2/2019 | ............. A61L 2/18 |
| DE | 102019118237 | A1 * | 1/2021 | |
| EP | 0602487 | A1 | 6/1994 | |
| EP | 1403187 | A1 * | 3/2004 | ............. B08B 3/02 |
| EP | 2556943 | A2 | 2/2013 | |
| JP | WO2002021583 | * | 1/2004 | ......... G03F 7/70741 |
| KR | 20090024580 | * | 3/2009 | .......... B65G 65/005 |
| WO | WO-2019029858 | A1 * | 2/2019 | ............. A61L 2/18 |

OTHER PUBLICATIONS

Robotic agricultural instrument for automated extraction of nematode cysts and eggs from soil to improve integrated (Year: 2021).*
Dynatect, Dyanamic equipment protection (Year: 2023).*
Dynatect, Dyanamic equipment protection (Year: 2023) (Year: 2023).*
ISA European Patent Office, International Search Report Issued in Application No. PCT/EP2018/064018, dated Oct. 10, 2018, WIPO, 4 pages.
China National Intellectual Property Administration, Office Action and Search Report Issued in Application No. 201880051250.4, dated Mar. 29, 2021, 19 pages. (Submitted with Machine Translation).

* cited by examiner

CONTAINER TREATMENT SYSTEM

CROSS-REFERENCE TO RELATED APPLICATIONS

The present application is a U.S. National Phase of International Patent Application Serial No. PCT/EP2018/064018 entitled "CONTAINER HANDLING SYSTEM," filed on May 29, 2018. International Patent Application Serial No. PCT/EP2018/064018 claims priority to German Patent Application No. 10 2017 213 861.0 filed on Aug. 9, 2017. The entire contents of each of the above-referenced applications are hereby incorporated by reference for all purposes.

The present disclosure pertains to a container treatment system.

BACKGROUND AND SUMMARY

Container treatment systems are sufficiently known from prior art. They can comprise several container treatment machines for the treatment of containers and are generally used in the beverage processing industry to manufacture, fill and pack containers.

Depending on the product to be filled or the additional cleanliness requirements, parts of the container treatment system, in particular individual container treatment machines, can be arranged in clean rooms. This applies in particular for filling machines and sealers, because the product can there come into contact with the ambient air, which leads to undesirable contamination.

If maintenance work is necessary at this container treatment machine, for example, in the course of a format changeover, opening the clean room and subsequent decontamination is necessary, so that the downtimes can be considerable there.

Object

Starting out from known prior art, the technical problem to be solved is therefore to specify a container treatment system with a container treatment machine in a clean room for which a time-saving format changeover can be carried out.

Solution

In one example, the issues described above may be at least partially solved by a container treatment system according to the present disclosure which is characterized in that it comprises a robot which is arranged in the clean room and is configured to exchange the exchangeable component.

In this context, "exchanging" a component means that a component arranged on the container treatment machine can be removed by the robot from the container treatment machine, and another component is mounted (in that place) on the container treatment machine.

In principle, the concept of component can be understood as being any part of the container treatment machine. However, this includes components to be exchanged, in particular in the case of format changeover, such as blow molds, sealers, sealing elements, nozzle tubes, guide members or supports.

Since the robot can exchange the exchangeable component without having to open the clean room, a format changeover can be performed quickly and in particular without opening and subsequently decontaminating the clean room, which can significantly reduce the downtimes of the container treatment system even for a changeover.

In one embodiment, the robot comprises a robotic arm that is fixedly mounted in the clean room or is arranged movable along a guide in the clean room. Depending on the requirements, different levels of freedom of motion can be ensured for the robot.

In one further development of this embodiment it can be provided that the guide and part of the robotic arm form a linear drive. They can be controlled very accurately and in an energy-efficient manner and configured to be free of lubricant which can reduce the risk of undesirable contamination of the clean room.

In one embodiment, it is provided that a magazine for the storage of exchangeable components is arranged in the clean room and the robot is designed to remove one of the exchangeable components from the magazine and attach it to the container treatment machine and to remove an exchangeable component attached to the container treatment machine from the latter and supply it to the magazine. Since the exchangeable components are already available to the robot in the clean room, the changeover at the container treatment system can there be carried out practically without interaction with the outside world, especially without physical interaction, which also reduces interaction with the operators.

In one alternative embodiment, a lock into which an exchangeable component can be inserted from outside the clean room is provided in the wall of the clean room, where the robot is designed to remove the exchangeable component from the lock and attach it to the container treatment machine and remove an exchangeable component attached to the container treatment machine from the latter and supply it to the lock. This allows, for example, for the introduction of new components previously not used in the container treatment system (for example, a new blow mold or a different sealing element) without the need to open the clean room. In this way, a flexible changeover can be achieved with at the same time low downtimes of the container handling system.

In one further development of this embodiment, it is provided that a sterilization device is arranged in the lock and can sterilize an exchangeable component introduced into the lock from outside the clean room. Unwanted contamination of the clean room can thus be prevented.

The exchangeable components can comprise at least one of sealing elements, bracket segments, slides or spike elements. These components are relatively small and lightweight and can therefore be moved by typically available robots even in a relatively small-sized clean room and attached to or removed from the container treatment machine.

In one embodiment, the robot is associated with a media passage for a liquid and/or gaseous medium, and a tool of the robot for exchanging the exchangeable component can be operated pneumatically or hydraulically by way of the medium. Alternatively or in addition, it can be provided that an electrical energy supply is associated with the robot and an electric motor is associated with a tool of the robot, so that the tool of the robot can be operated by the electric motor.

The media supply can be designed and suitable for the delivery of a gaseous as well as a liquid medium. Alternatively, two media passages can be provided, where one of these passages delivers a liquid and the other a gaseous medium. The combination with the electric motor for operating the tool can also pertain to the same tool that can be operated pneumatically or hydraulically by said medium. The same tool can then also be controlled with different degrees of accuracy or performance. Alternatively, one or more tools of the robot can be operated pneumatically or hydraulically, whereas other tools of the robot in this embodiment are operated by use of one or more electric motors.

In one further embodiment, the robot comprises a nozzle and is designed to act upon the container treatment machine with a medium, for example, for lubricating or cleaning components. In addition to the format changeover, other maintenance work can then also be carried out at the container treatment machine without the need for the clean room to be opened.

The method according to the invention for exchanging exchangeable components of a container treatment machine arranged in a clean room for the treatment of containers, such as bottles, in the beverage processing industry, where a robot is arranged in the clean room, comprises that the robot removes an exchangeable component of the container treatment machine from the container treatment machine and exchanges it for a different exchangeable component. The components therefore remain in the clean room or can be removed from the clean room via a lock without having to open the clean room to the outer atmosphere for a format changeover. Downtimes during format changeover can thus be reduced.

In a further development of this method, the robot first removes the exchangeable component from the container treatment machine and guides it to a magazine for exchangeable components or a lock in the wall of the clean room accessible from outside the clean room and then collects the other exchangeable component and then attaches this other exchangeable component to the container treatment machine. This process is particularly effective in terms of time, which can further reduce the possible downtimes of the container treatment system during the changeover process.

In one further embodiment, the robot is moved along a guide between a first position and a second position at least during the exchange of the exchangeable component. It is there not necessary to move the entire robot, but only a part of the robot, for example a robotic arm, can be moved along such a guide. This embodiment enables reaching many different positions in the container treatment machine and thereby the replacement of different exchangeable components.

Furthermore, it can be provided that the robot cleans and/or lubricates at least one component of the container treatment machine by acting upon it with a medium from a nozzle of the robot. In this way, further maintenance and/or cleaning work at the container treatment machine, in addition to the format changeover, can be carried out in a time-saving manner.

In one further embodiment, the exchangeable component is exchanged by the robot in a fully automated manner or controlled by an operator from outside the clean room. The first alternative can entail saving further time, whereas operator control also allows surprising events to be managed when changing formats or during other functions.

In one embodiment, it is provided that the exchange of the exchangeable component takes place during a standstill of the container treatment machine or during a treatment step of a container in the container treatment machine which does not use the exchangeable component.

The "standstill" of the container treatment machine is there to be understood such that the latter does not treat the containers during a certain period of time, for example several minutes or hours, and that no movement of components takes place, i.e. the machine is in fact at a standstill or does not produce, respectively.

Treatment steps not using an exchangeable component to be exchanged is to be understood as being such a phase in the movement of the container treatment machine, which, depending on the throughput of the container treatment machine, can take a few seconds or a few minutes and during which the respective component is neither used nor moved. Alternatively, such process control which uses different components in a temporally alternating manner (for example, different filling members of the container treatment machine) is also possible there.

DETAILED DESCRIPTION

Figure 1:
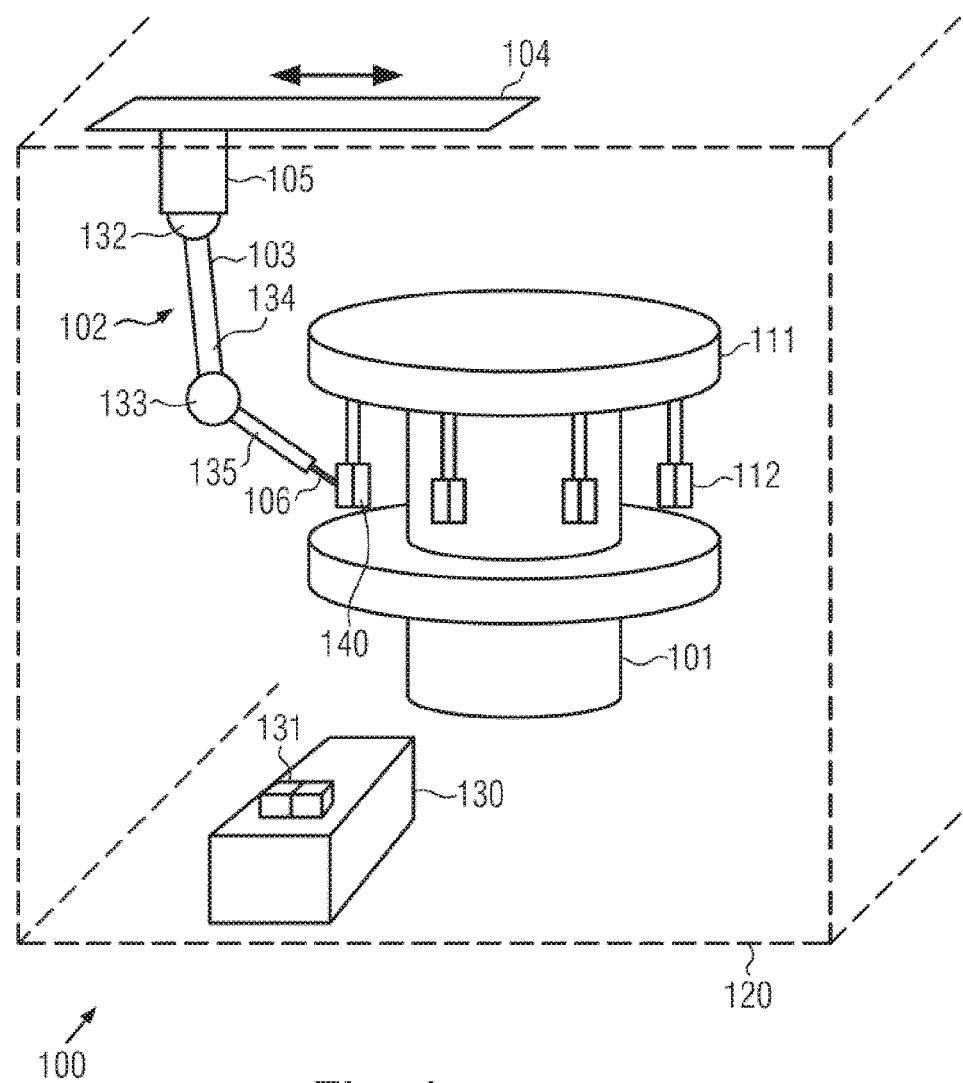
FIG. 1 schematic representation of a container treatment system according to one embodiment FIG. 2 schematic representation of a container treatment system according to a further embodiment.

FIG. 1 shows schematic representation of a container treatment system 100 according to one embodiment. The container treatment system in this embodiment comprises a clean room 120 in which a container treatment machine 101 is arranged. This container treatment machine can be any machine commonly employed in the beverage processing industry. In particular fillers that fill a product into a container can be considered. Similarly, preferably mold filling machines can be considered, in which the product is likewise introduced into the preforms for molding the preforms to the finished container. In principle, any container treatment machine treating a container or preforms with an interior space open to the environment can be arranged in clean room 120.

In the embodiment presently shown, the container treatment machine comprises a carousel 111 on which several container treatment stations 112 are arranged.

The embodiment shown there is of course not mandatory. Even if presently not shown, it is provided that the container treatment machine has some kind of communication through the wall of clean room 120 via which containers from outside clean room 120 can be supplied to container treatment machine 101 without impairing the controlled atmosphere within clean room 120. For example, a lock, presently not shown, can be provided through which containers can be guided continuously or cyclically into the clean room and supplied via suitable transport devices to container treatment machine 101.

According to the invention, a robot 102 is further arranged in clean room 120. This robot is configured to exchange one component, for example component 140, of container treatment machine 101 for a further component.

For this purpose, a magazine 130, in which or on which one or more further exchangeable components 131 are stored, is provided in this embodiment. In the embodiment shown in FIG. 1, robot 102 can therefore remove component 140 from container treatment machine 101 and deliver it to magazine 130. Furthermore, the robot can remove one of exchangeable components 131 stored in magazine 130 from the magazine and supply it to container treatment machine 101.

The exchangeable components can be a wide variety of components, in particular relatively small components. These include blow molds and sealing elements or sealing devices. Further includes are bracket segments or slides and spike elements. Other relatively small and lightweight components as well can be exchanged by the robot, depending on the demand and configuration of the container treatment machine. Robot 102 can be configured, in particular, to transport and exchange components (i.e. attach or remove them from container treatment machine 101) having external dimensions of up to 50×50×50 cm and a weight of up to 30 kg.

In the embodiment presently illustrated, robot 102 comprises a robotic arm 103 which can be attached, for example, to a support 105 of the robot. Robotic arm 103 can comprise several joints 132 and 133 and several segments 134 and 135, each connected to at least one of the joints. The joints can be rotatable, pivotable, or movable in any other way, so that different segments 134 and 135 can be moved relative to each other.

Robotic arm 103 is preferably connected via a joint to support 105. Support 105 can either be fixedly mounted in clean room 120 or be mounted movable along a guide 104. Guide 104 can be a stator, so that guide 104 and support 105 together form a linear drive. This has the advantage that lubricants can be avoided to the degree possible and contamination of clean room 120 can then be prevented. The attachment of the robotic arm by way of support 105 to guide 104 also allows for an increase in the range of motion of robot 102. While the robotic arm in the embodiment presently shown is illustrated as being movable along a guide arranged at the "ceiling" of clean room 120, this is not mandatory. Guide 104 can be arranged, for example, on one of the side walls or on the ground of clean room 120. The latter variant offers the advantage that any leaking lubricants or similar substances can be extracted directly, for example, in designated openings or containers on the ground, thereby reducing the risk of contamination of containers treated in the container handling machine.

Also the embodiment of guide 104 as a substantially straight element is not mandatory. The guide can have, for example, a curvature or extend, for example, snaking along the ceiling of clean room 120, so that an area of clean room 120 as large as possible can be covered by robot 102.

If, for example, the container treatment machine is configured as a rotary machine, as presently shown, it can be provided that the guide is configured such that robot 102 can reach any place at the perimeter of the container treatment machine or at the perimeter of carousel 111.

Alternatively or in addition, it can also be provided that the carousel of the container treatment machine can be moved in a clocked manner so that one or more components to be exchanged are by successive rotation of the carousel successively moved to a position in which robot 102 can reach and exchange them. The guide in this embodiment does not have to lead around the entire container treatment machine, but can also be formed only around a part or along a part of the perimeter, or robot 102 can be firmly arranged in the clean room, for example, by way of support 105.

For the embodiment presently shown, but also for all other embodiments described below, robot 102 can act either autonomously or at least partially autonomously or be controlled by an operator, preferably from outside the clean room. In the first example, robot 102 can be associated with a processor unit which is preferably configured as artificial intelligence and has a memory in which several motion profiles are stored which can be retrieved according to the requirement profile (component to be exchanged and related actions) and converted into a motion of the robot.

If robot 102 is controlled by an operator, it is provided that a control terminal is arranged, preferably located outside clean room 120, so that the robot can be controlled without the need to open the clean room. The control terminal can be connected to robot 102 via a data line, preferably also a wireless connection, so that control signals can be exchanged.

Similarly, robot 102 can have suitable sensors that allow determining the position of the robot relative to components or other objects within the clean room.

It can furthermore be provided that the robot comprises suitable devices for self-cleaning (not shown). For example, if robot 102 (as described in FIG. 3) is equipped with a nozzle with which it can clean components of the container treatment machine, then the robot can further be configured in such a way that it can at least in part self-clean. Dedicated cleaning devices on the robot are presently also conceivable.

Figure 2:
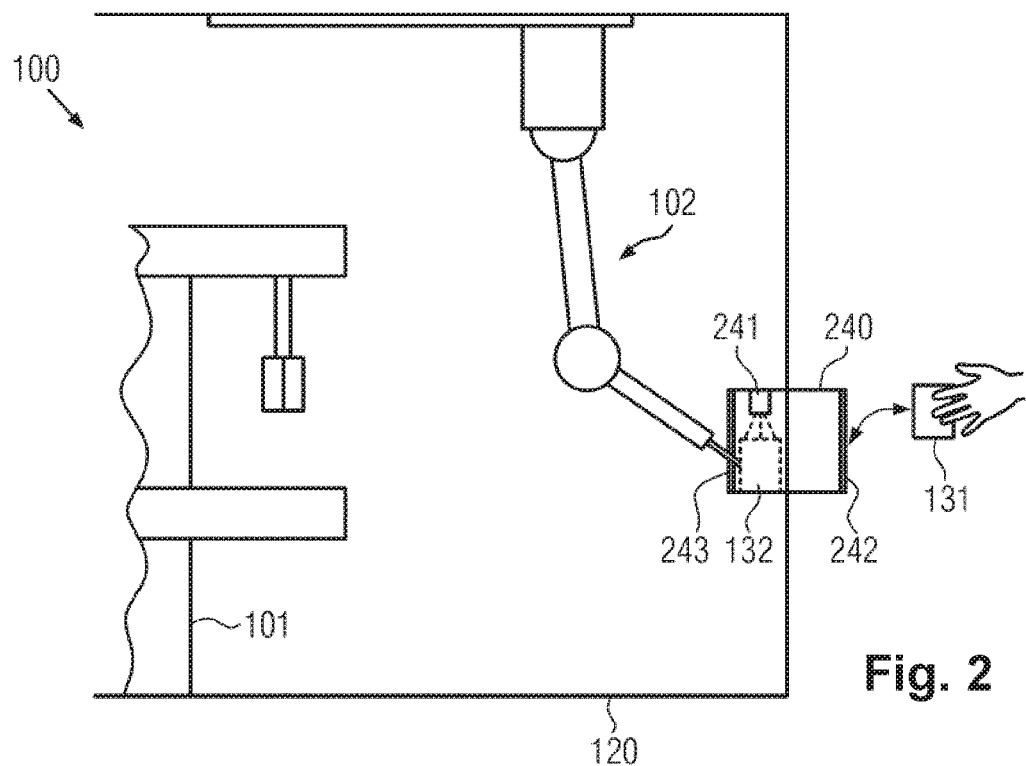

FIG. 2 shows an embodiment alternative to the embodiment shown in FIG. 1 for supplying exchangeable components. In the embodiment presently shown, a lock 240 is arranged in the wall of clean room 120. This lock allows the interior of clean room 120 to be in communication with the outer environment of the clean room. This communication is preferably not permanently open, but the lock disposes of lockable entrances 242 and 243, which can be formed, for example, as doors. It can be provided that mechanical measures or control system measures are taken to prevent the doors from opening at the same time. This ensures that only door 243 or door 242 is open and that contamination of the interior of clean room 120 is prevented.

Furthermore, it can be provided that a sterilization device is arranged in the lock and can sterilize an exchangeable component 132 introduced into the lock. Sterilization device 241 can be formed, for example, comprising one or more nozzles which can introduce a sterilization medium, preferably a liquid or gaseous medium, into the region of lock 240 while openings 242 and 243 are closed, in order to sterilize the atmosphere within lock 240 as well as component 132 introduced thereinto. For example, the action of a sterilizing medium, such as hydrogen peroxide, can take place. The introduction of peracetic acid in liquid form or as a mist is also conceivable.

In any case, robot 102 is configured in such a way that it can first remove from the lock an exchangeable component 131 which has been introduced by an operator into lock 240, and can then supply or attach it to container treatment machine 101. The same applies, of course, to an exchangeable component attached to the container treatment machine 101 which is to be removed from the container treatment machine. In this case, robot 102 removes this exchangeable component from the container treatment machine and places it through opening 243 into lock 240, from where it can then be removed by an operator via opening 242. In such a case, the sterilization of the exchangeable component or the atmosphere prevailing in the lock after introduction of the exchangeable component by robot 102 into lock 240 can be dispensed with since the risk of contamination of the interior of clean room 120 is no longer given. Nevertheless, it can be partially desirable to sterilize the exchangeable component, which is possible according to the previously described method with the aid of the sterilization device.

Figure 3:
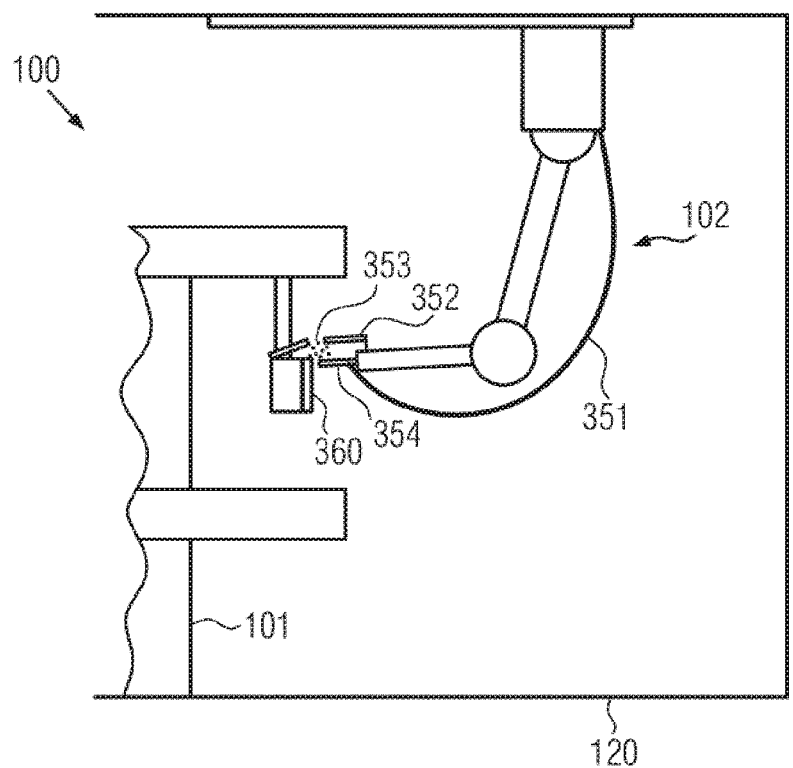
FIG. 3 schematic representation of a container treatment system with a robot

FIG. 3 shows a further embodiment, in particular of robot 102, as part of container treatment system 100.

In the embodiment presently shown, the robot disposes in particular of a tool 354 with which it can interact with components to be exchanged, but also with other parts of the container treatment machine, in such a way that the disassembly and installation of an exchangeable component is possible. For example, this tool can be a gripper. The embodiment is also not restricted to a single tool, so that, for example, a kind of screwdriver can be provided to loosen screw connections and, furthermore, the gripper described can be provided to grip the exchangeable component and to remove it from or attach it to the container treatment machine.

One or more tools can be driven by suitable drives. For example, one or more electric motors can be provided on or in robot 102 and be associated with a corresponding tool 354 and actuated to cause the latter's movement or interaction with other components of the container treatment machine. In particular, the electric motors can be servomotors with a high degree of response accuracy.

Alternatively or in addition, one or more media passages 351 can be provided which are in communication, for example, on one side with an actuatable pump and on the other side establish a connection to tool 354. By having a medium act upon these lines (for example liquid or gas), pneumatic or hydraulic operation of tool 354 can take place.

Alternatively or in addition to this embodiment, it can be provided that robot 102 comprises a nozzle 352 via which a medium 353, for example, a sterilizing medium such as hydrogen peroxide, or a sterilizing liquid, such as peracetic acid, can be output to sterilize either one of the exchangeable components or a further component of the container treatment machine. In addition or alternatively, for example, a lubricant can be applied via a suitable nozzle and lubricate components or exchangeable components of the container treatment machine should this be necessary. This nozzle can also be advantageously used to enable autonomous cleaning of the robot. For this purpose, the robot can move the robotic arm in such a way that the nozzle is moved over one or more of the robot's components so that the medium can be applied to them by nozzle 352.

The invention claimed is:

1. A container treatment system for the treatment of containers, in the beverage processing industry, comprising:
   a clean room and a container treatment machine arranged therein with at least one exchangeable component, wherein said container treatment system comprises a robot which is arranged in said clean room and is designed to exchange said exchangeable component, wherein said robot comprises a robotic arm, which is arranged as movable along a guide arranged at a ceiling or a ground of said clean room, wherein said guide and a part of said robot form a linear drive, wherein the robotic arm comprises several joints and several segments, each connected to at least one of the joints, wherein the joints are rotatable and pivotable, and wherein the guide comprises a curvature.

2. The container treatment system of claim 1, wherein a magazine for the storage of exchangeable components is arranged in said clean room and said robot is designed to remove one of said exchangeable components from said magazine and attach it to said container treatment machine and said robot is also designed to remove another exchangeable component attached to said container treatment machine and supply the another exchangeable component to said magazine.

3. The container treatment system of claim 1, wherein a lock, into which an exchangeable component is inserted from outside said clean room, is provided in the wall of said clean room, and wherein said robot is designed to remove said exchangeable component from said lock and attach it to said container treatment machine and said robot is also designed to remove another exchangeable component attached to said container treatment machine and supply the another exchangeable component to said lock.

4. The container treatment system of claim 3, wherein a sterilization device is arranged in said lock and configured to sterilize the exchangeable component inserted into said lock from outside said clean room.

5. The container treatment system of claim 4, wherein said exchangeable component is one of a sealing element, a bracket segment, a slide, and a spike element.

6. The container treatment system of claim 3, wherein said robot is associated with a media passage for a liquid medium or a gaseous medium and a tool of said robot is operated pneumatically or hydraulically by said liquid medium or the gaseous medium for exchanging said exchangeable component, and/or wherein an electrical energy supply is associated with said robot and an electric motor is associated with a tool of said robot, so that said tool of said robot can be operated by said electric motor.

7. The container treatment system of claim 3, wherein said robot comprises a nozzle designed to act upon said container treatment machine with a medium for lubricating or cleaning components.

8. A method for exchanging exchangeable components of a container treatment machine arranged in a clean room for the treatment of containers, in the beverage processing industry, comprising:
   removing an exchangeable component of the exchangeable components of the container treatment machine from the container treatment machine via a robot arranged in said clean room; and
   exchanging the exchangeable component for a different exchangeable component via the robot, wherein the robot comprises a robotic arm, wherein said exchanging further comprises moving the robotic arm between a first position and a second position along a guide arranged at a ceiling or a ground of said clean room, wherein said guide and a part of said robot form a linear drive, wherein the robotic arm comprises several joints and several segments, each connected to at least one of the joints, wherein the joints are rotatable and pivotable, and wherein the guide comprises a curvature.

9. The method of claim 8, wherein the removing further comprises said robot first removing said exchangeable component from said container treatment machine and guiding said exchangeable component to a magazine, and wherein the magazine is configured for storing the different exchangeable component.

10. The method of claim 8, further comprising cleaning and lubricating at least one component of the container treatment machine via the robot, wherein the robot comprises a nozzle configured to act on the at least one component with a liquid medium or a gaseous medium.

11. The container treatment system of claim 3, wherein an electrical energy supply is associated with the robot and an electric motor is associated with a tool of the robot, so that the tool of the robot is operated by said electric motor.

12. The method of claim 8, wherein the removing further comprises the robot removing the exchangeable component from the container treatment machine and guiding the exchangeable component to a lock in the wall of a room accessible from outside of the clean room.

13. The method of claim 8, further comprising collecting the different exchangeable component via the robot and subsequently attaching the different exchangeable component to the container treatment machine.

14. The method of claim 8, wherein the exchanging via the robot is fully automated.

15. The method of claim 8, wherein the exchanging via the robot is controlled by an operator from outside the clean room.

16. The method of claim 8, wherein the exchanging of the exchangeable component takes place either during a standstill of the container treatment machine or during a treatment step of a container in the container treatment machine, wherein the treatment step does not use the exchangeable component.

17. A system, comprising:
- a clean room comprising a ceiling and walls for separating an interior volume of the clean room from an area outside of the clean room;
- a container treatment system configured to treat bottles configured to store liquids; and
- a robot comprising a robotic arm, which is arranged as movable along a guide arranged at one of the ceiling or a first wall of the walls and configured to actuate in response to feedback from a sensor or an input provided via an operator from outside of the clean room, wherein the guide comprises a curvature, wherein the robot is configured to arrange a first exchangeable component within a lock arranged in a second wall of the walls via moving from a first position to a second position, and wherein the robot acquires a second exchangeable component from the lock when in the second position.

\* \* \* \* \*